United States Patent
Ghiassi et al.

(10) Patent No.: US 11,534,152 B2
(45) Date of Patent: Dec. 27, 2022

(54) STABILIZING RETRACTOR SYSTEM FOR DISTAL RADIUS FRACTURE REPAIR

(71) Applicant: RetractOrtho, Inc., Solano Beach, CA (US)

(72) Inventors: Alidad Ghiassi, Los Angeles, CA (US); Steven Howard, La Jolla, CA (US); Bradley Klos, Solana Beach, CA (US); Michael Bauschard, Richmond, VA (US)

(73) Assignee: RETRACTORTHO, INC., Solana Beach, CA (US)

( * ) Notice: Subject to any disclaimer, the term of this patent is extended or adjusted under 35 U.S.C. 154(b) by 0 days.

(21) Appl. No.: 17/685,271

(22) Filed: Mar. 2, 2022

(65) Prior Publication Data
US 2022/0183672 A1    Jun. 16, 2022

Related U.S. Application Data

(63) Continuation of application No. 17/368,623, filed on Jul. 6, 2021.

(Continued)

(51) Int. Cl.
*A61B 17/02* (2006.01)
*A61B 17/17* (2006.01)
(Continued)

(52) U.S. Cl.
CPC ........ *A61B 17/025* (2013.01); *A61B 17/1782* (2016.11); *A61B 17/8897* (2013.01);
(Continued)

(58) Field of Classification Search
CPC .................. A61B 17/025; A61B 17/1782
See application file for complete search history.

(56) References Cited

U.S. PATENT DOCUMENTS

| 3,731,673 A | 5/1973 | Halloran |
| 3,766,910 A * | 10/1973 | Lake .................. A61B 17/0206 606/198 |

(Continued)

FOREIGN PATENT DOCUMENTS

| CN | 206434403 | 8/2017 |
| CN | 207125751 | 3/2018 |
| EP | 0731669 | 9/1996 |

*Primary Examiner* — Christian A Sevilla
(74) *Attorney, Agent, or Firm* — Knobbe, Martens, Olson & Bear LLP

(57) ABSTRACT

A stabilizing retractor system for distal radius fracture repair includes a backing plate configured to support the back of the wrist and having a first side accessible on a first side of the wrist, a second side accessible on a second side of the wrist. A first soft tissue retractor is engageable with the backing plate and has a first radius engaging concavity on a first side, and a first soft tissue retracting surface on a second side. A second soft tissue retractor is engageable with the backing plate and has a second radius engaging concavity on a first side, and a first soft tissue retracting surface on a second side. The first and second tissue retractors may be advanced apart from each other to retract tissue, and retained by a tie which connects the first and second retractors around the back of the backing plate.

20 Claims, 16 Drawing Sheets

Related U.S. Application Data

(60) Provisional application No. 63/050,633, filed on Jul. 10, 2020.

(51) Int. Cl.
  *A61B 17/88* (2006.01)
  *A61B 17/00* (2006.01)

(52) U.S. Cl.
  CPC ............... *A61B 2017/0092* (2013.01); *A61B 2017/00862* (2013.01)

(56) References Cited

U.S. PATENT DOCUMENTS

| | | |
|---|---|---|
| 4,938,230 A | 7/1990 | Machek et al. |
| 5,334,194 A | 8/1994 | Mikhail |
| 5,512,038 A * | 4/1996 | O'Neal ............... A61B 17/0206 600/210 |
| 5,520,608 A | 5/1996 | Cabrera |
| 6,190,312 B1 | 2/2001 | Fowler, Jr. |
| 6,409,731 B1 | 6/2002 | Masson |
| 7,195,593 B1 * | 3/2007 | Masson ............... A61B 17/025 600/210 |
| 8,905,923 B2 | 12/2014 | Carlson |
| 9,414,827 B2 | 8/2016 | Salomon |
| 2005/0080320 A1 | 4/2005 | Lee |
| 2005/0085723 A1 * | 4/2005 | Huebner ............... A61B 90/39 600/431 |
| 2006/0019216 A1 * | 1/2006 | Priluck ............... A61C 5/90 433/140 |
| 2008/0021286 A1 | 1/2008 | Risto et al. |
| 2011/0054262 A1 | 3/2011 | Cobb |
| 2012/0283519 A1 | 11/2012 | Nguyen et al. |
| 2017/0202672 A1 | 7/2017 | Persaud |
| 2018/0338807 A1 | 11/2018 | Kim et al. |
| 2019/0374214 A1 | 12/2019 | Bohl |
| 2020/0253595 A1 * | 8/2020 | McBride, Jr. ......... A61B 34/30 |
| 2022/0008054 A1 * | 1/2022 | Ghiassi ............... A61B 17/02 |

* cited by examiner

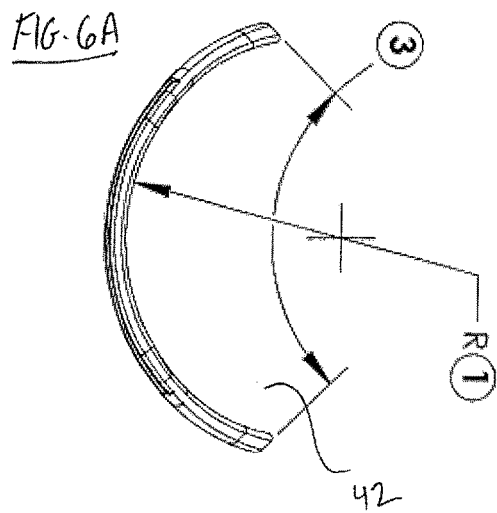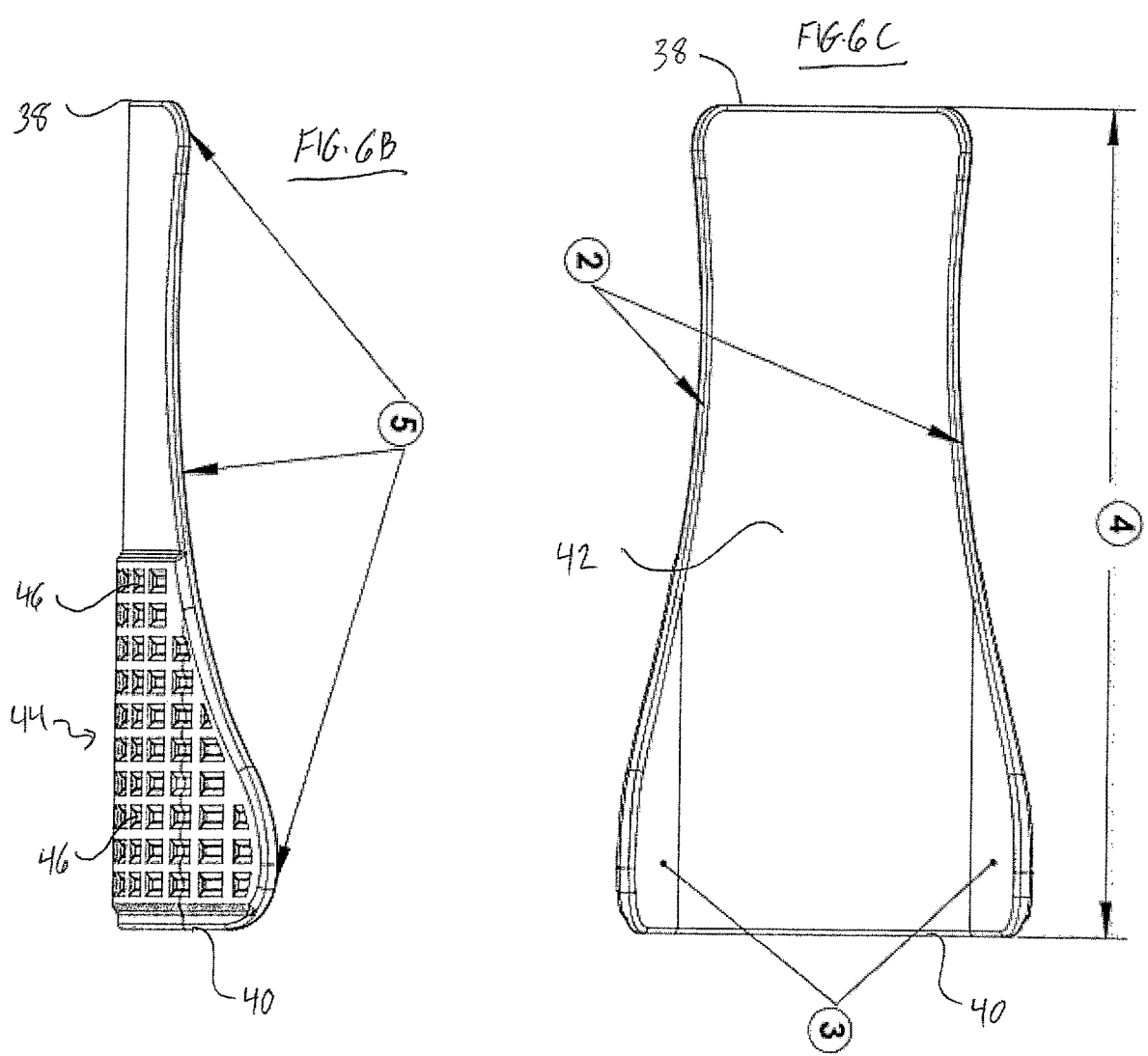

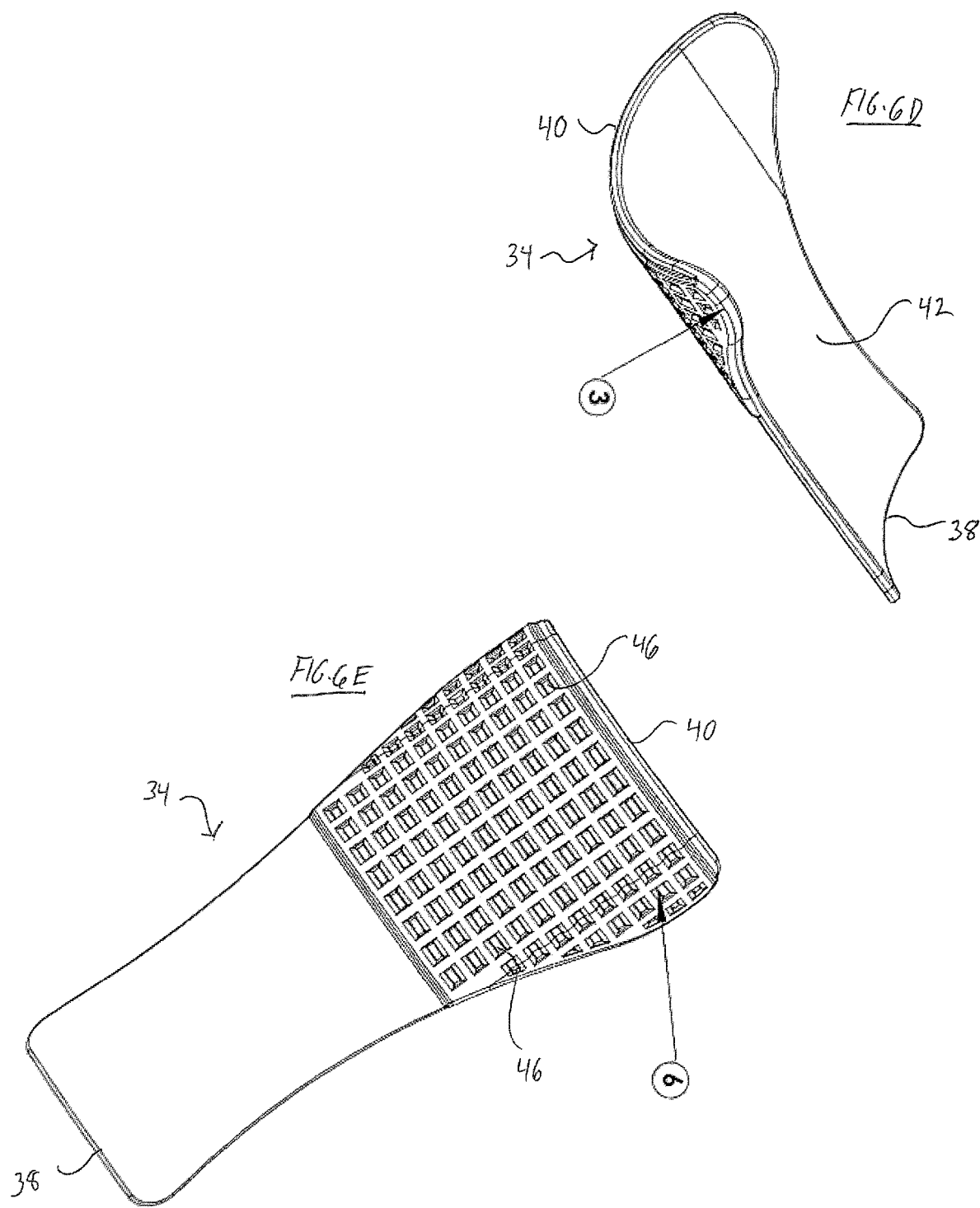

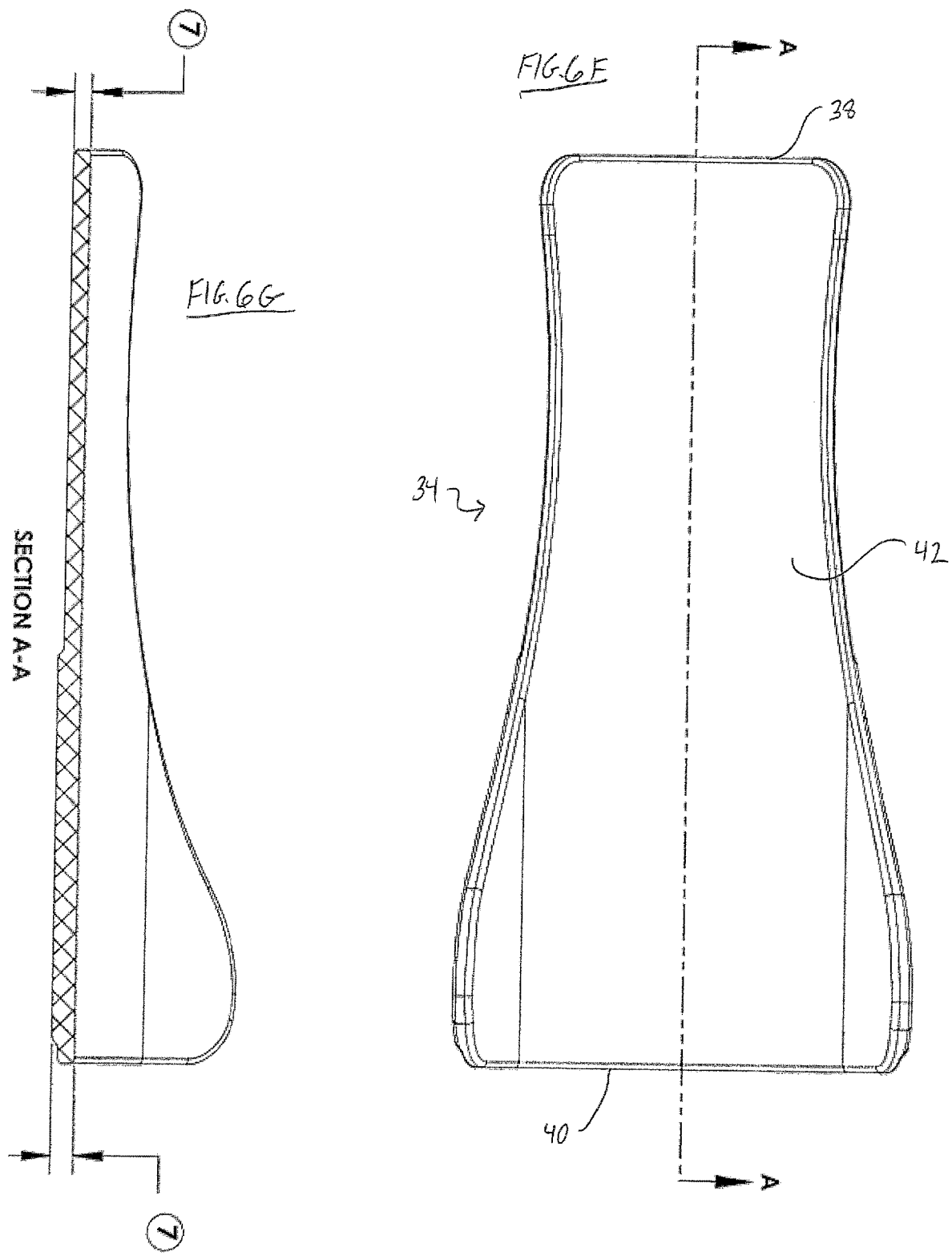

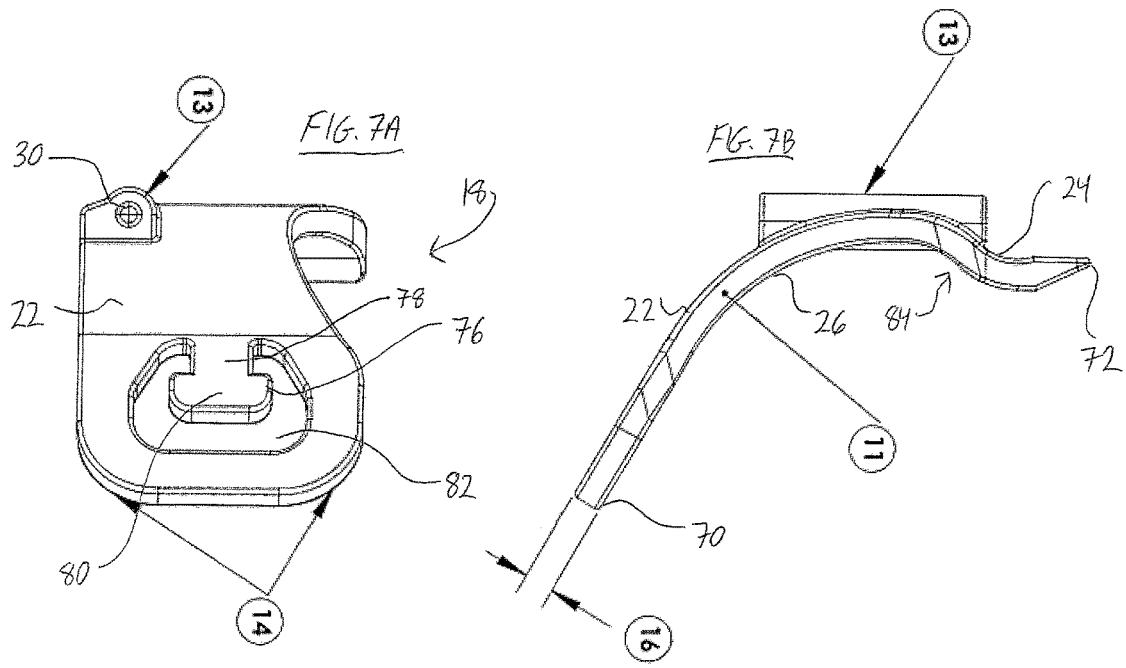
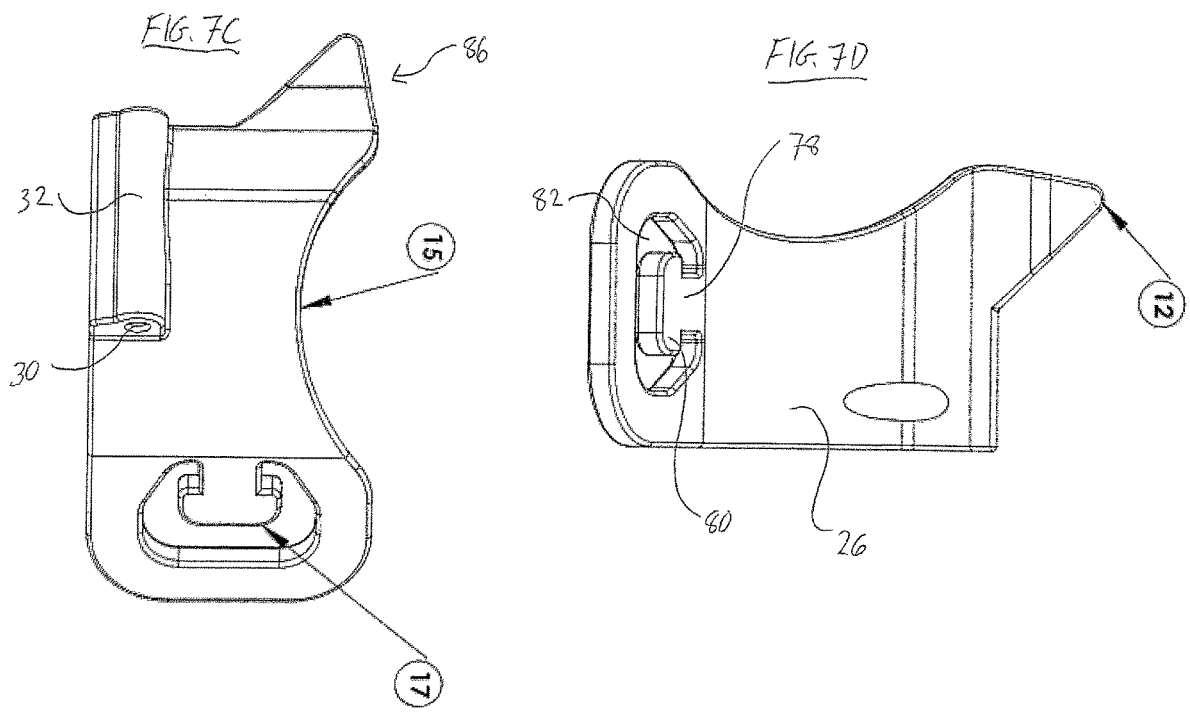

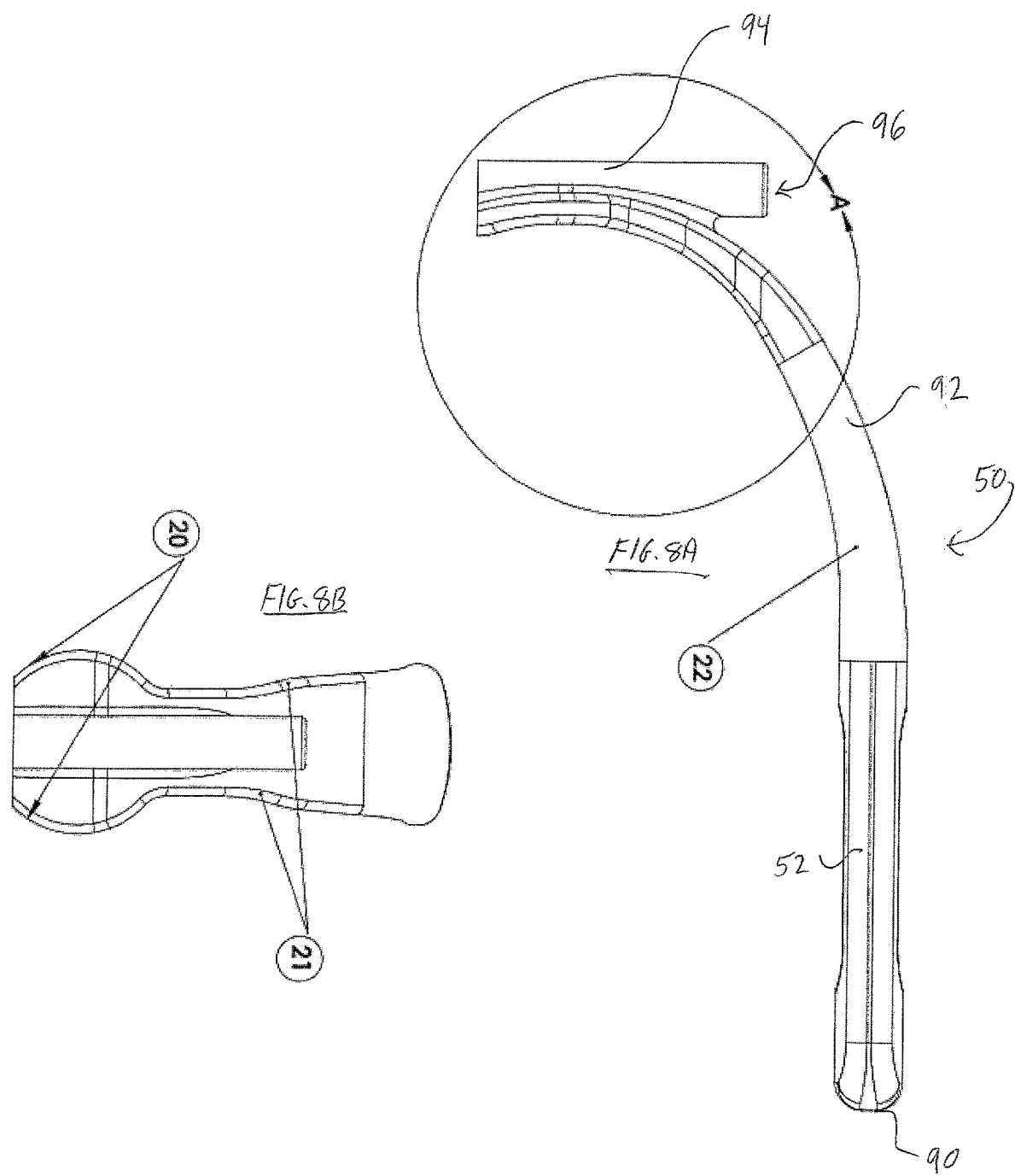

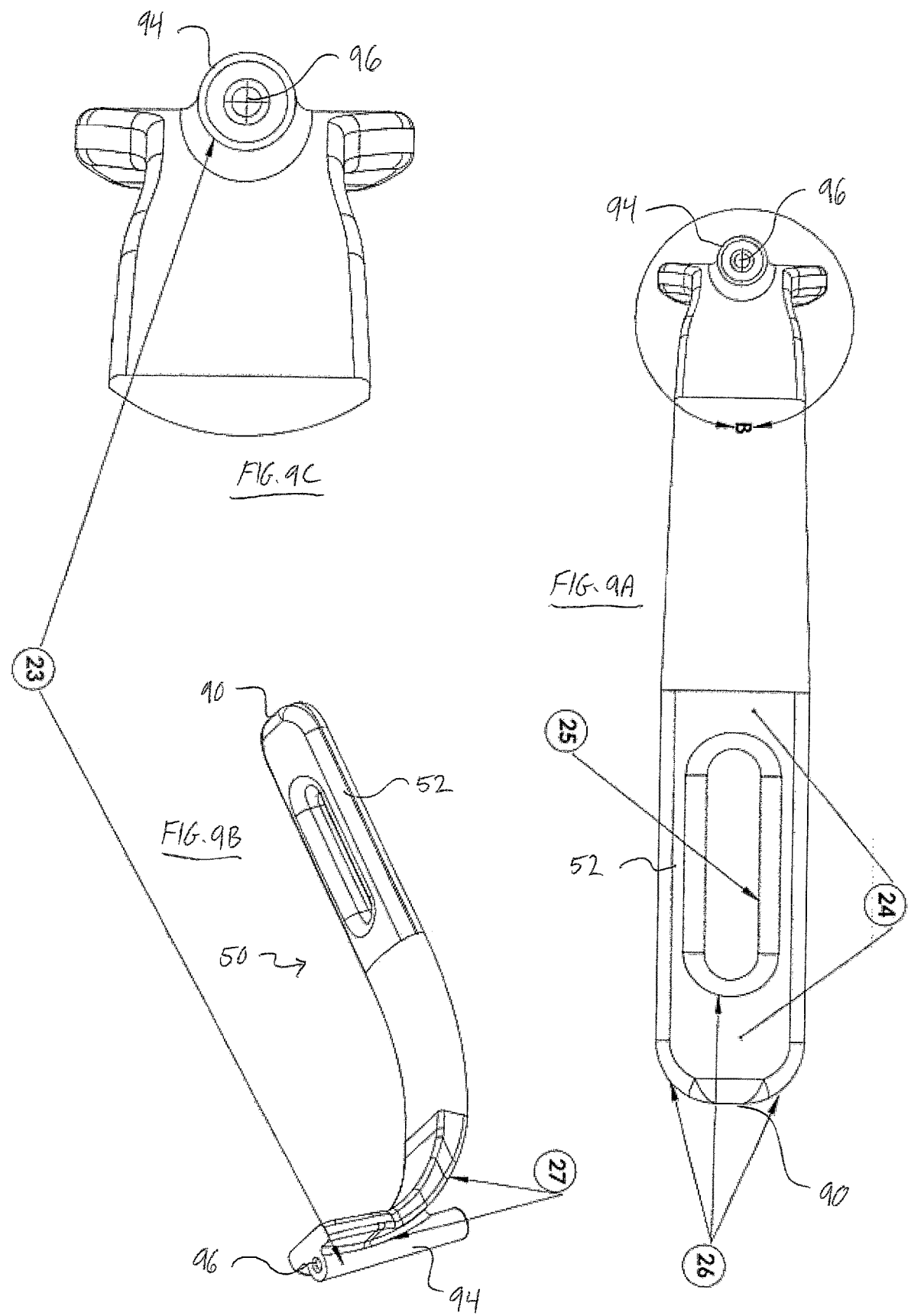

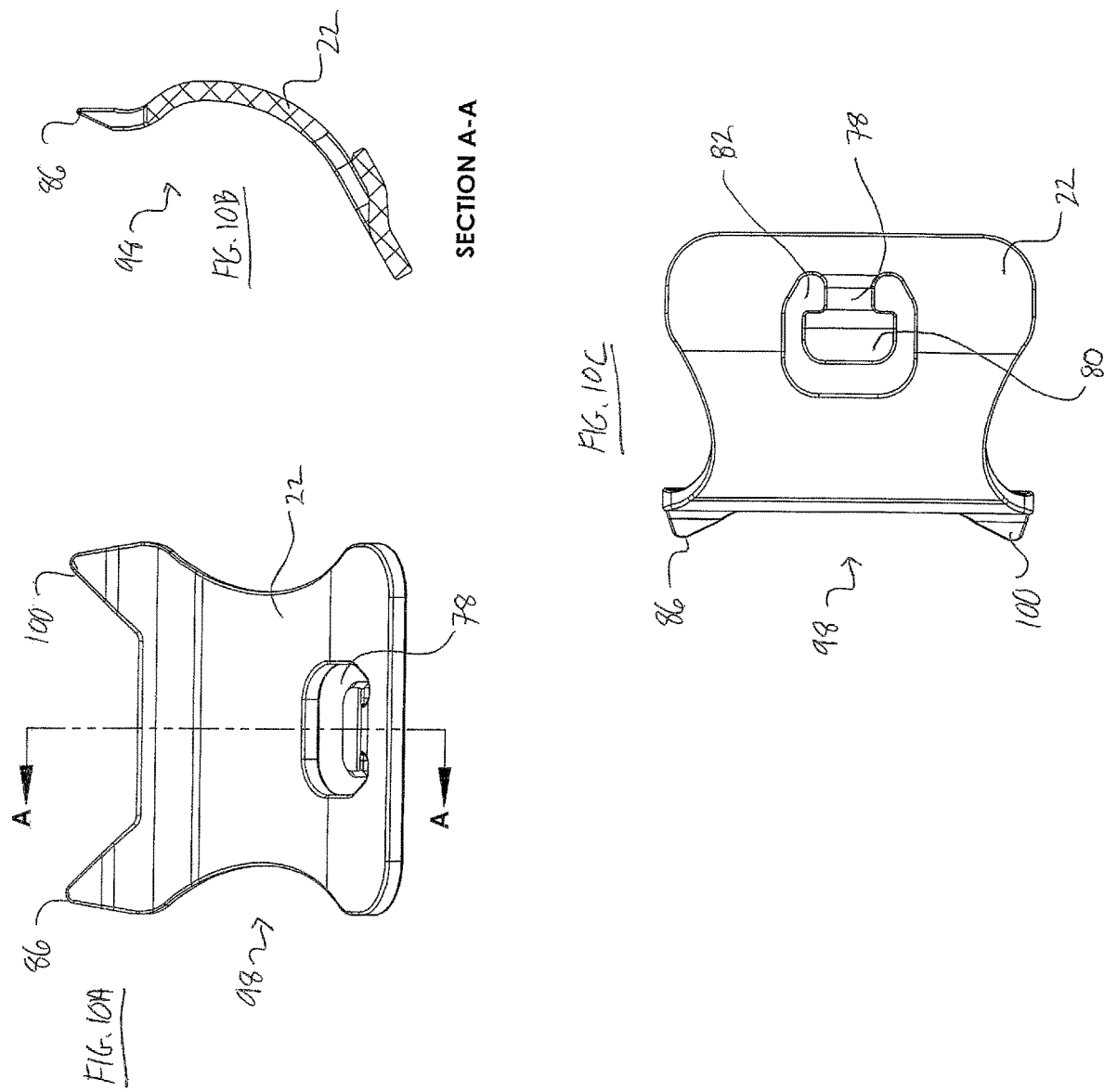

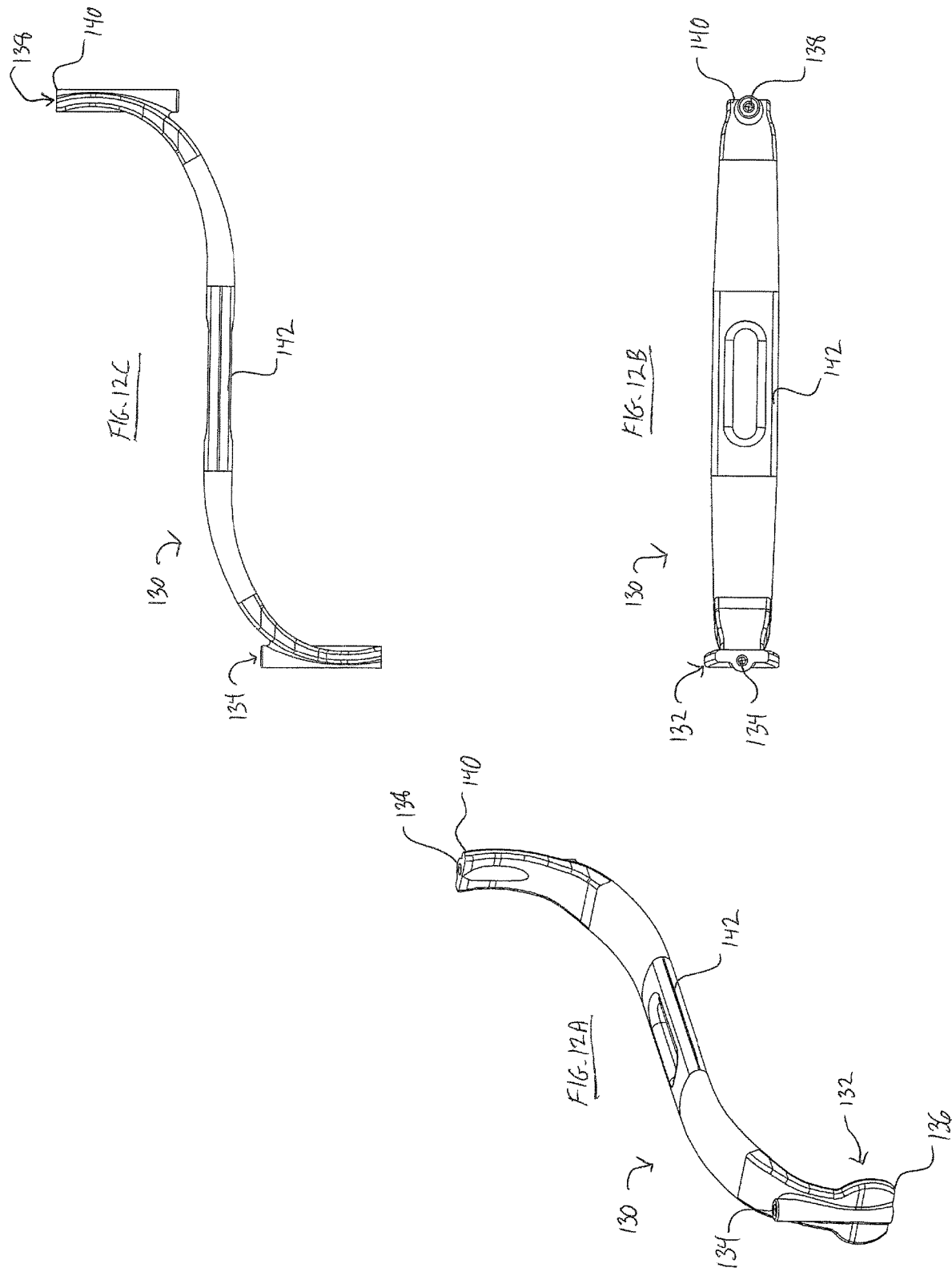

STABILIZING RETRACTOR SYSTEM FOR DISTAL RADIUS FRACTURE REPAIR

CROSS-REFERENCE TO RELATED APPLICATIONS

This application is a continuation of U.S. patent application Ser. No. 17/368,623, filed on Jul. 6, 2021, which claims the priority benefit under 35 U.S.C. § 119(e) of U.S. Provisional Application No. 63/050,633, filed Jul. 10, 2020, the entireties of which are hereby incorporated by reference herein.

BACKGROUND OF THE INVENTION

A distal radius fracture is one of the more common hand and wrist surgeries performed. Treatment often requires attachment of a surgical implant to bone structures for adding strength. The surgical procedure for addressing this type of fracture can be complicated due to the number and proximity of adjacent structures, such as muscles, ligaments, tendons, and blood vessels that surround this area. The corresponding procedure requires that the tissues and muscles in the wrist be moved so that the bone can be exposed. Various surgical retraction tools are available to manipulate tissues and anatomical structures during surgery. Conventional retractors include manual articulated or rigid elongation members for positioning the adjacent anatomy by manual operation by a surgeon or assistant.

The standard surgical approach to the distal radius is the volar approach which involves making an incision on the volar aspect (the palm side) of the forearm at the wrist level. This allows for a safe and extensile exposure of the fractured aspect of the distal radius, allowing for reduction of the fracture and placement of hardware to retain the fracture in its correct or reduced position. Most commonly this involves using a plate and screws. The challenge here is that there are numerous structures that run longitudinally down the arm into the hand, and traverse the surgical field. These need to be retracted and protected in order for the procedure to be performed safely and efficiently. There are two types of surgical retractors: handheld devices which require surgeon or assistant to hold in one hand, and self-retaining retractors which do not need to be held in position manually, once they are inserted into the wound.

Notwithstanding the foregoing, there remains a need for an improved retraction system which stabilizes a joint during surgical repair, for any of a variety of joints and bones, including, among others, in the wrist, the Radius, Ulna and carpals and in the ankle, the Tibia and Fibula.

SUMMARY OF THE INVENTION

Systems are disclosed for stabilizing bones or bone fragments during surgical reduction of a fracture and installation of fixation hardware. Although discussed herein primarily in the context of wrist repair, the stabilizing systems of the present invention may be utilized in a variety of other procedures, in which stabilization and tissue retraction may be desirable, including particularly the ankle repair of either the tibia or fibula.

In accordance with one aspect of the present invention, there is provided a stabilizing retractor system for distal radius fracture repair. The system comprises a backing plate configured to support the back of the wrist, the backing plate having a first side accessible on a first side of the wrist, a second side accessible on a second side of the wrist and a longitudinal axis. At least a first soft tissue retractor is also provided, comprising a first support body having a first radius engaging concavity on a first side and on a distal portion of the body and a first soft tissue retracting surface on a second side, and proximal to the first radius engaging concavity.

The stabilizing retractor system may further comprise a second soft tissue retractor, comprising a second support body having a second radius engaging concavity on a first side and a second soft tissue retracting surface on a second side. The system may further comprise a guide on the first soft tissue retractor, configured to direct a wire across the first radius engaging surface. The guide may comprise a lumen, which may extend through the first support body, or may extend through a guide structure carried by the first support body. The lumen may extend along an axis that intersects the surface of the radius in the intended use orientation at an angle that is within about 15 degrees of perpendicular to the surface of the radius, and in some implementations the axis is substantially perpendicular to the surface of the radius.

The system may additionally comprise a connector on a proximal portion of each of the first and second soft tissue retractors, and a tie for attaching the connectors around a back of the wrist and biasing the proximal ends of the first and second soft tissue retractors apart from each other. The tie may be elastic.

The backing plate may have a convex side and a concave side, and may have first and second opposing forceps landing zones on the convex side, configured to facilitate grasping of the retractor system with forceps. The landing zones may comprise an anti slip surface for enhancing attachment of the forceps, which may be a plurality of surface deviations such as a plurality of projections or a plurality of recesses or a plurality of apertures.

There is also provided a soft tissue retractor, having an elongate, curved support body having a proximal end and a distal end and a curved long axis that exceeds the length of a short, transverse axis. A radius engaging concavity may be located on a first side of the body in a distal portion of the body. A concave soft tissue retracting surface may be provided on a second side of the body, and proximal of the radius engaging concavity. An inflection point may occur on the body in between the radius engaging concavity and the soft tissue retracting surface. The inflection point may occur in the distal one half of the body, or in the distal one third or one quarter of the length of the body.

A guide may be provided for guiding a pin over the radius engaging concavity to engage the radius when positioned within the radius engaging concavity. The guide may comprise a lumen. A connector may be provided on the body spaced apart proximally from the radius engaging concavity, for connection to a tie.

Preferably the body is radiolucent, enabling the reduced and stabilized wrist and attached retractor system to be moved as a unit for Xray imaging, and moved back out again without disrupting the orientation of the bones and retractor system.

There is also provided a stabilizing retractor kit. The kit may include a backing plate; a first and second soft tissue retractors; and a tie for connecting the first and second soft tissue retractors. The kit may also include a drill guide.

There is also provided a method of treating a distal radius fracture. The method comprises positioning a backing plate with a wrist contacting front surface and a back surface along the back of a wrist. A distal end of a first soft tissue retractor is engaged with a first side of a radius, and a distal end of a second soft tissue retractor is engaged with a second side of the radius. A proximal end of the first soft tissue retractor and a proximal end of the second soft tissue retractor are moved away from each other to retract opposing sides of an incision; and the first and second soft tissue retractors are connected to retain the incision open. The connecting step may comprise connecting the first and second soft tissue retractors with a tie extending around the back surface of the backing plate. The tie may bias the proximal ends away from each other, and may be elastic. The method may additionally comprise the step of anchoring the first and second soft tissue retractors to the radius.

The method may additionally comprise the step of moving the patient's wrist with the attached stabilizing retractor system into an Xray or other imaging modality field of view, and inspecting the fracture without the stabilizing retractor system blocking any of the image of the fracture and adjacent bones. The wrist may then be moved back out of the imaging field of view for further steps, without having disturbed the fracture. Further steps may include adjustment or installation of fixation hardware, further adjustment of the fracture or removal of the stabilizing retractor system and closure of the surgical site.

There is also provided a method of retracting soft tissue from an incision site to expose a bone. The method may comprise engaging a distal end of a first soft tissue retractor with a first side of the bone, and engaging a distal end of a second soft tissue retractor with a second side of the bone. A proximal end of the first soft tissue retractor and a proximal end of the second soft tissue retractor are moved away from each other to retract opposing sides of an incision; and the first and second soft tissue retractors are connected to retain the incision open. The connecting step may comprise connecting the first and second soft tissue retractors with a tie. The tie may bias the proximal ends of the first and second soft tissue retractors away from each other to retract tissue away from the incision. The tie may be elastic. The method may additionally comprise the step of anchoring the first and second soft tissue retractors to the bone.

The method may further comprise the step of imaging the bone through the retractors with the retractors anchored to the bone, at one or more times during the procedure, enabled by the radiolucent material of the retractors. The method may further comprise the step of reducing two adjacent bone fragments to form a union and placing a plate over the union. The method may additionally comprise the step of clamping the plate against the union and moving the plate, soft tissue retractors and union into an X-ray beam. The clamping step may comprise providing a clamp having a first jaw and a second jaw, placing the first jaw against the plate and placing the second jaw against a convex side of a backing plate attached to the first and second soft tissue retractors. The clamp may then be used to move the retractors, plate and union away from a surgical table, into and out of an X-ray beam and back to the surgical table while maintaining the spatial relationship of the union, plate and retractors without relative movement. In one implementation of the invention, the plate is a volar plate.

In any of the systems and methods disclosed herein, a retractor can be left side or right side specific, or universal to both sides. The retractor may be configured with or without a lumen, and can have a single distal tip or two or more distal tips to facilitate insertion and prying.

A number of the steps in the procedure can be varied in accordance with clinical preference. For example, if the K-wire is placed first, a twisting motion of the left and right retractors opens the incision to facilitate placing the distal tip. If the tip is anchored first and then the retractor is retracted back against soft tissue before placing the K-wire, the surgeon will have better visualization for the K-wire placement in the bone.

In some applications of the method, the bone may be a radius, ulna, or carpals in the wrist or a fibula or a tibia in the ankle.

BRIEF DESCRIPTION OF THE DRAWINGS

FIGS. 6A-6G are detail views of a backing plate.

FIGS. 7A-7D are detail views of a soft tissue retractor.

FIGS. 8A-8B are detail views of a drill guide.

FIGS. 9A-9C are additional detail views of a drill guide.

FIGS. 10A-10C are detail views of a soft tissue retractor configured for use on the fibula.

FIGS. 12A-12C illustrate a dual headed lunate anchor and drill guide.

DETAILED DESCRIPTION OF THE PREFERRED EMBODIMENT

Figure 1:
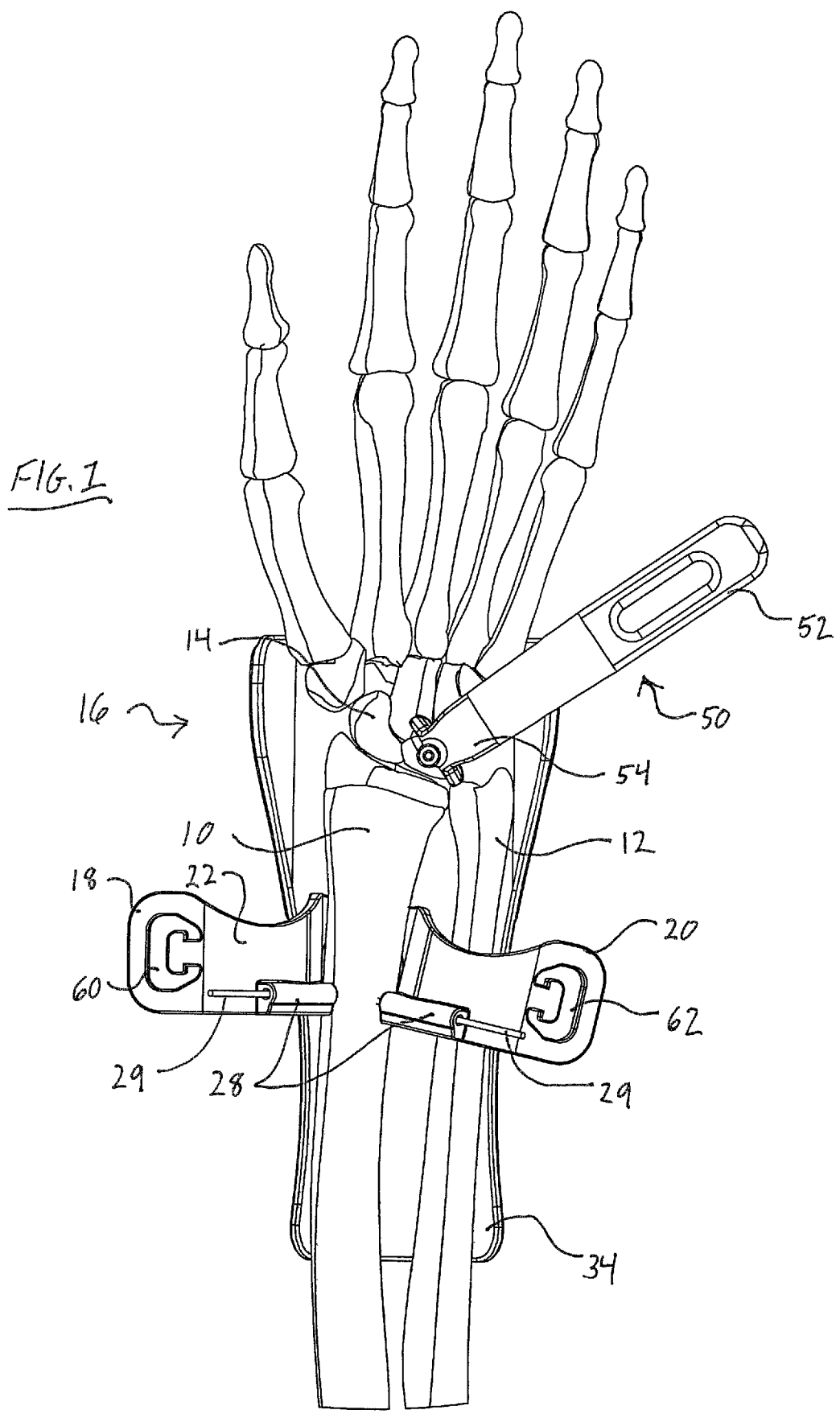
FIG. 1 is a schematic representation of a stabilizing retractor system attached to a radius.
Figure 2:
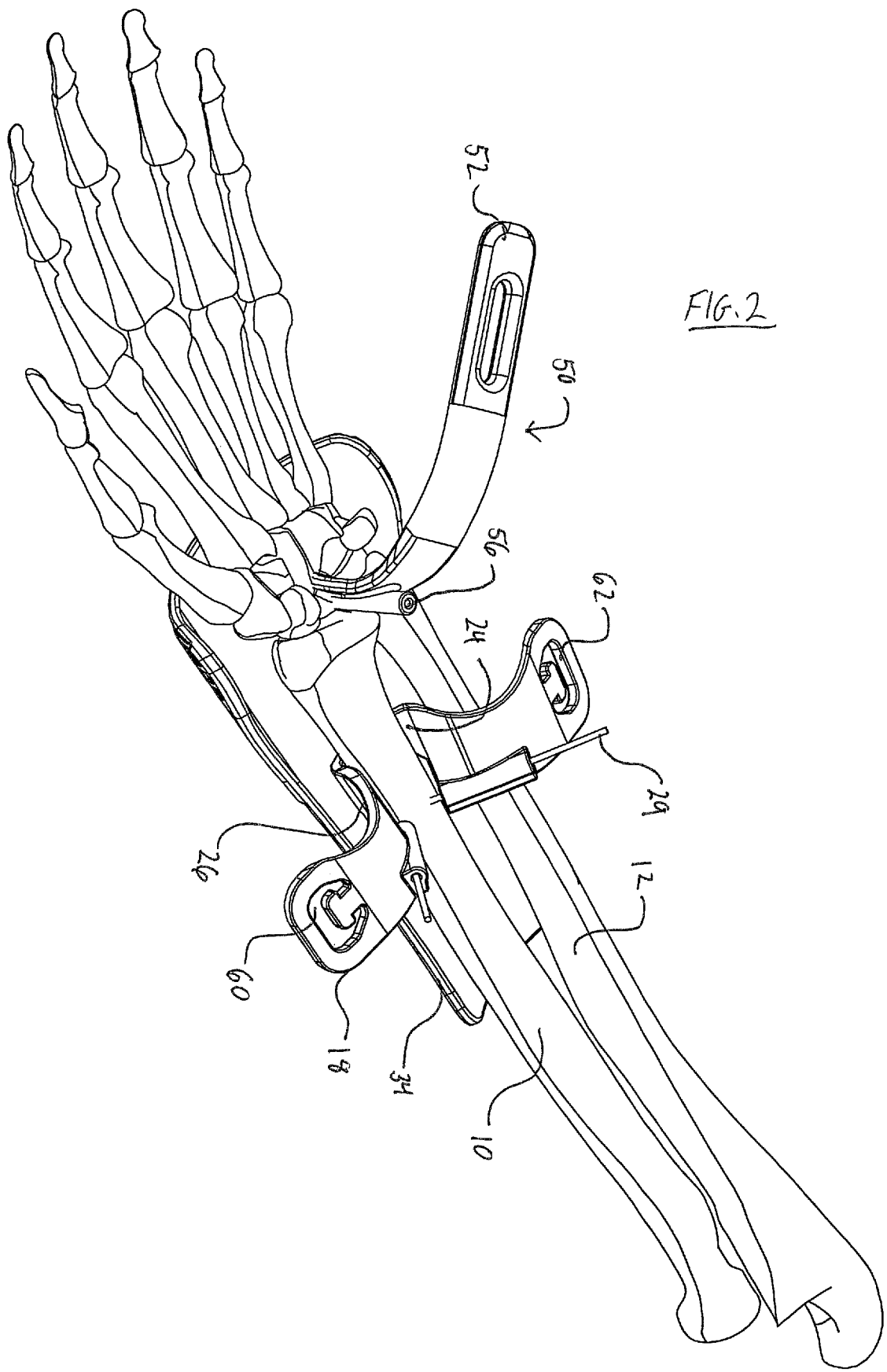
FIG. 2 is a perspective view of the system of FIG. 1.
Figure 3:
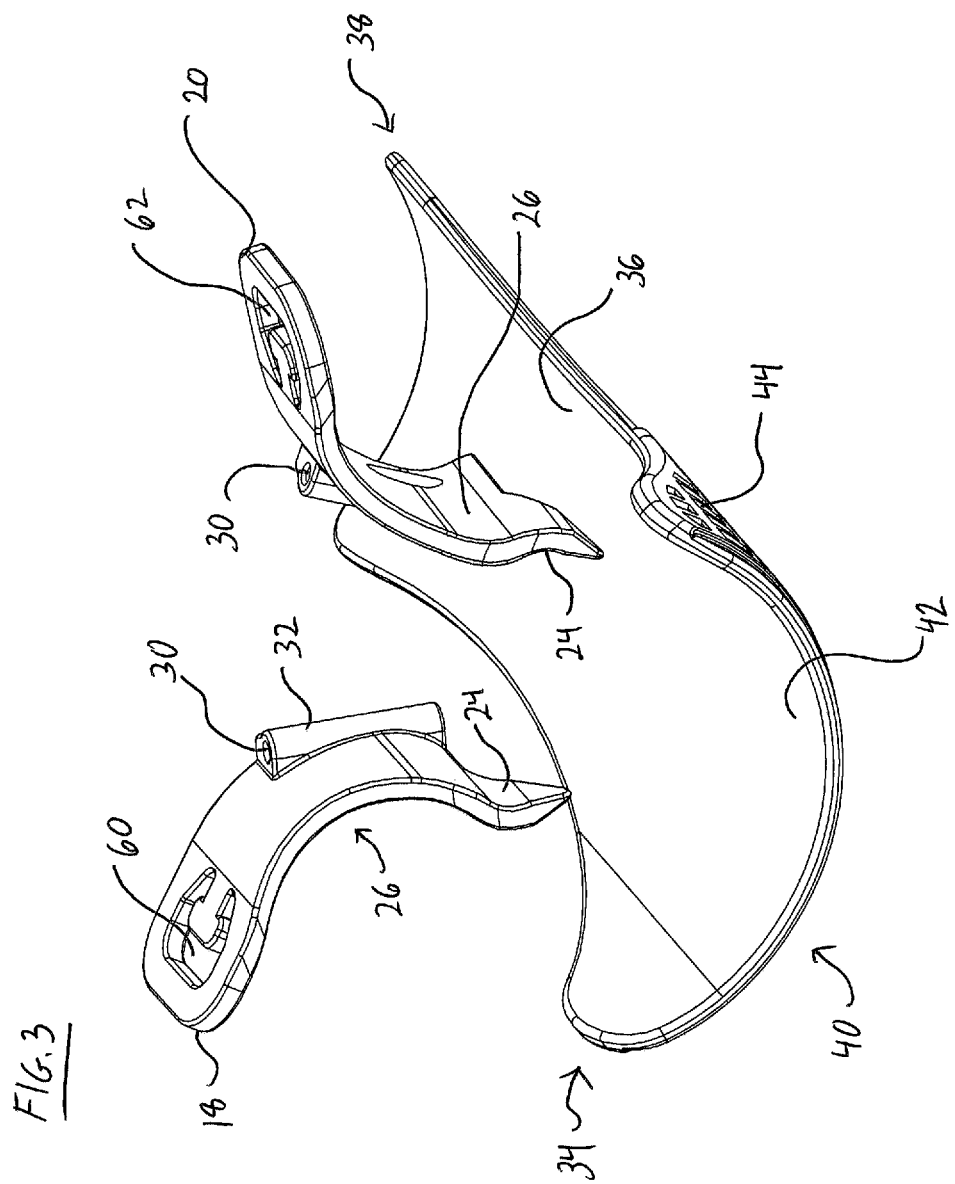
FIG. 3 is an exploded perspective view of a backing plate and two soft tissue retractors.
Figure 4:
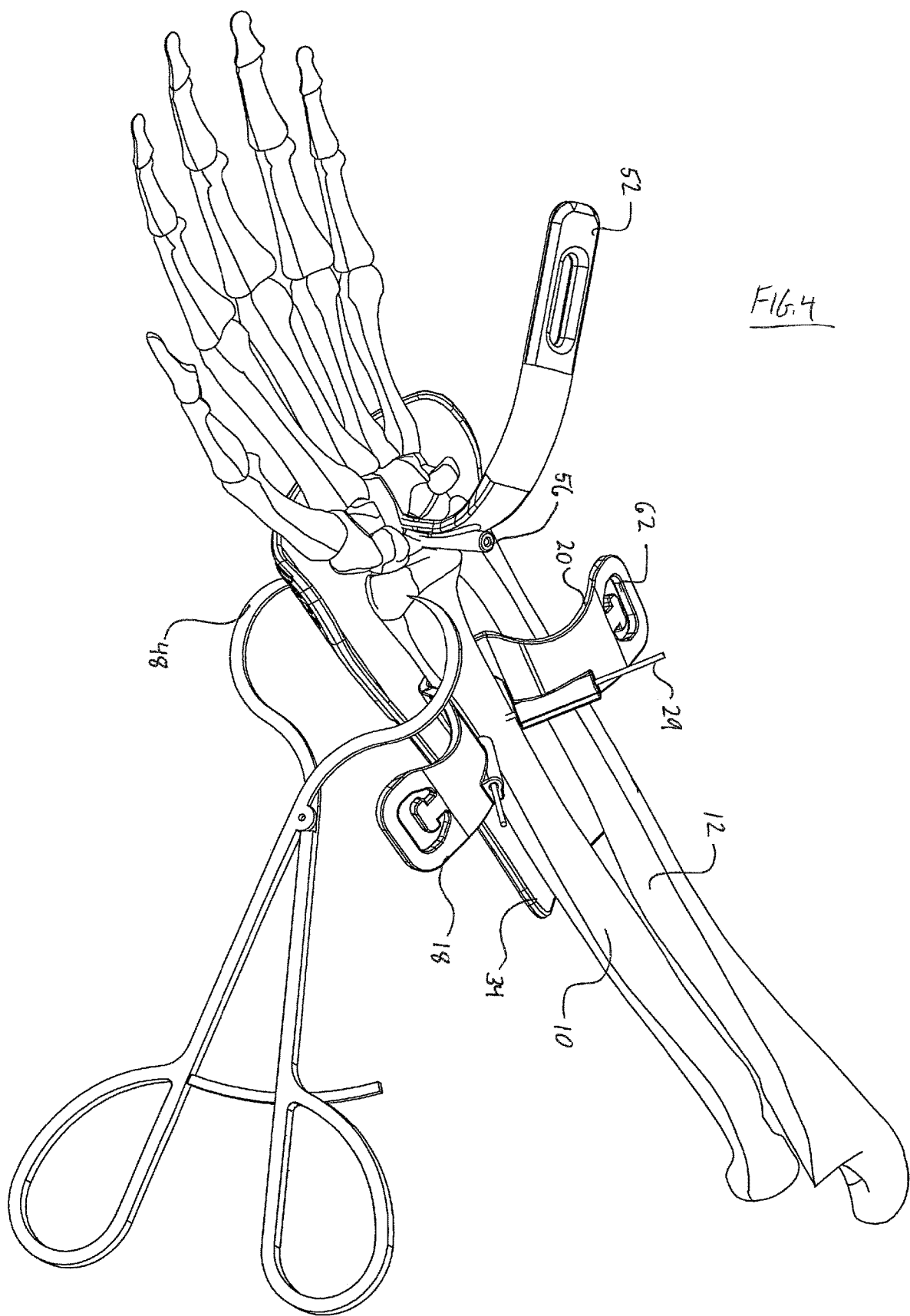
FIG. 4 is a top perspective view as in FIG. 2, shown being grasped by forceps.

The stabilizing retractor system of the present invention enables a surgeon to place a joint or limb in a pre-determined position, retract tissue from an incision site, and stabilize the retractors by securing them to an adjacent bone. This eliminates the need for additional clinical personnel to hold the retractors. Although the system described herein can be readily adapted to other surgical procedures throughout the body, it will be detailed herein primarily in the context of wrist or hand surgery as an example. The invention can be readily expanded to multiple other areas with elbow, shoulder, knee, ankle (Tibia and Fibula), and hip surgery being of particular emphasis.

In the context of a wrist surgery, the stabilized retractors also allow the surgeon to manipulate the wrist and location of an implant into a desired orientation, and move the wrist into and out of an X-ray field of view while maintaining the relative orientation of the wrist and of the implant relative to adjacent bone. This enables fine adjustments to the implant based upon the X-ray image since the orientation of the wrist and implant is maintained by the stabilized retractors.

The system may be constructed of radiolucent plastic components that can be fabricated through 3D printing or other more traditional methods like injection molding or thermo-forming. Components may be packaged for a single patient procedure and pre-sterilized. Components may be single use only and disposable.

During the surgical procedure, the clinician will position a primary support shell underneath the limb or joint to be accessed. The clinician will make an incision and then utilize a first and second opposing retractors retract the tissue. The retractors are next fixed with respect to adjacent bone to maintain the retracted tissue. Fixation may be accomplished by pinning each retractor to the radius using at least one K-wire per retractor.

It is likely that each system will thus include 1 support shell and 2 retractors. Each system may be configured with more components based upon customization. The additional components may include, for example, wire or wraps to secure the retractors adequately to the patient, and one or more elastic ties to secure the retractors to the support shell. The components may have attachment anchor guides such as holes and slots as necessary to allow for complementary attachment anchors or attachment to other components.

Customization for use in complicated cases may occur by 3D printing of parts based upon scanned image data on a patient by patient basis. Customization could also be more generic to a particular surgical procedure.

Conventional retractors are metallic and therefore impervious to X-ray imaging. This has impact to the Clinician, the assistant, and the patient. The clinician routinely risks chronic exposure to radiation through repeated exposure of hands during examination of the patient. The assistant has similar risk. Routinely, the assistant and clinician will remove the retractors so that imaging of the reduced bone union and implants can be clearly seen. When the retractors are removed, the clinician or assistant must insert their hands into the x-ray field to try to keep the fracture stable. Maintaining the union stable is not always achieved, potentially requiring additional repositioning and imaging steps. Also, with repeated insertion and removal of the retractors, there is increased risk to nerve and tendons that are repeatedly stretched and manipulated by rigid metallic retractors.

Referring to FIG. 1, there is illustrated a simplified view of the volar aspect of the forearm at the level of the wrist, including a radius 10, an ulna 12, and a scaphoid 14. Numerous additional small bones in the wrist and hand are not discussed herein but are understood in the art.

A stabilizing retractor system 16 in accordance with the present invention is illustrated as mounted to the radius 10. Surrounding soft tissue has been omitted for clarity, however the retractor system 16 will be utilized to separate opposing soft tissue sides of a surgical cut down to expose the radius 10 as is understood in the art.

The system 16 includes a first retractor 18 and a second complementary retractor 20. The second retractor 20 may be a mirror image and/or have similar functionality to the first retractor 18, so primarily only a single retractor will be described in detail.

Retractor 18 comprises a support 22 such as a contoured plate, which will be described in greater detail below. In general, the support 22 includes a radius engaging surface 24 on a first side of the support 22, and a soft tissue retracting surface 26 on a second, opposite side of the support from the radius engaging surface 24. The retractor may be characterized as having a long axis and a transverse short axis Support 22 additionally comprises a guide 28 defining a lumen 30 for axially movably receiving an attachment pin 29 such as a K wire, for securing the support 22 to the radius 10. The lumen 30 may extend directly through the support 22, or extend through a separate guide structure 32 carried by the support 22. The lumen 30 may be oriented to receive the K wire along a path that is substantially perpendicular to the adjacent surface of the radius 10 in the as mounted orientation. The axis of the guide 28 is generally within about 20 degrees, in many implementations within about 15 degrees or 10 degrees or less of parallel to the long axis. In the illustrated configuration, the guide 28 is substantially parallel to the long axis.

The retractor system may additionally comprise a backing plate 34, for positioning on the opposite side of the wrist from the incision. The backing plate may comprise an elongate arcuate body 36 having an (anatomically as used) proximal end 38, a distal end 40, and an elongate concavity 42 for receiving the wrist.

Figure 5:
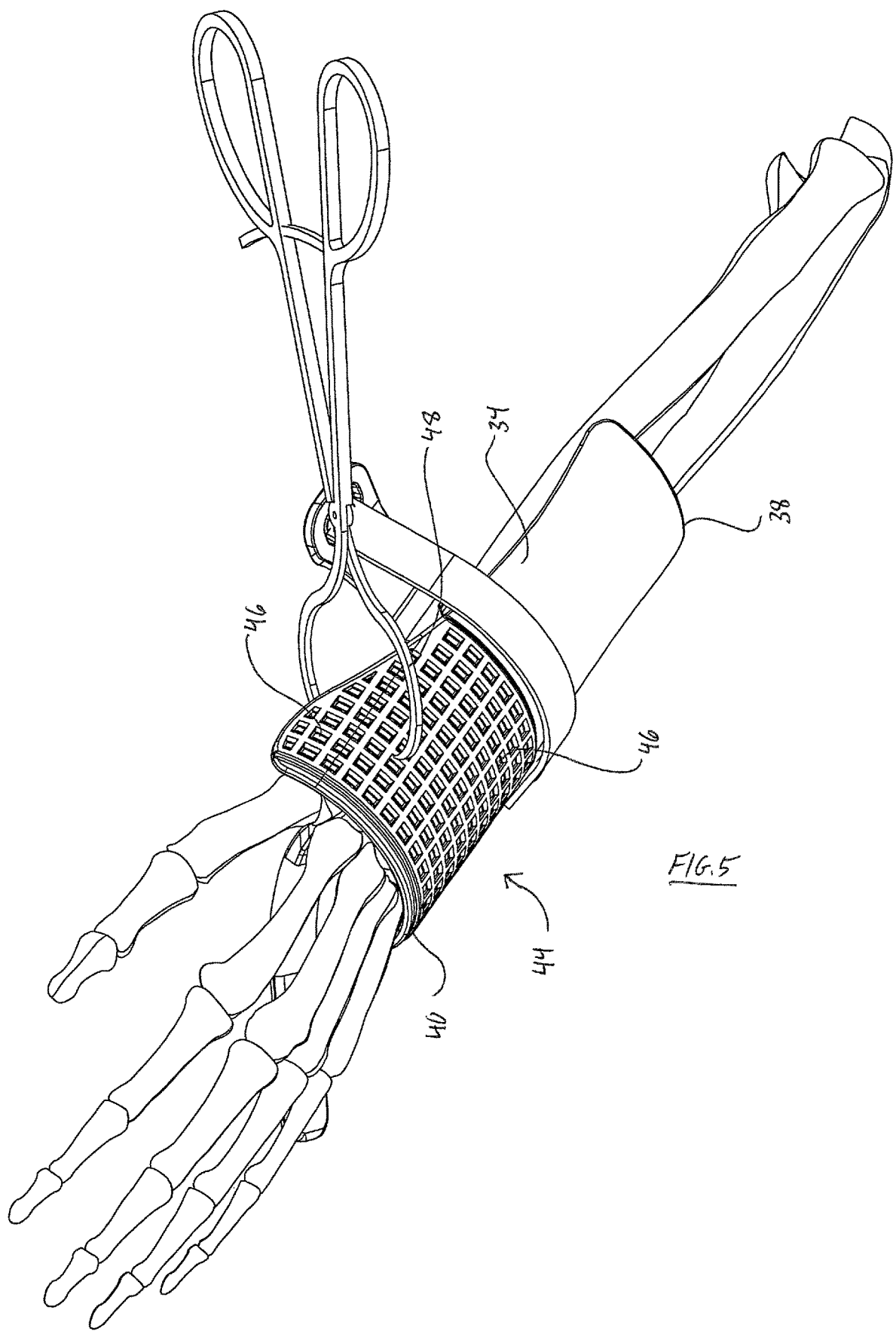
FIG. 5 is a bottom perspective view as in FIG. 2, shown being grasped by forceps.

A convex side of the body 36 may be provided with a forceps landing zone 44, comprising a plurality of recesses 46 for receiving a forceps prong 48 as shown in FIG. 5. At least about 10 or 20 or 50 or more recesses 46 may be provided to produce a large landing zone so that the surgeon will obtain first try engagement of the forceps with the blind side of the backing plate 34 when grasping the stabilized wrist with the forceps such as to move it into a visualization (X-Ray) field and back to the table.

The system 16 may additionally include a drill guide 50 having a proximal handle 52 and a distal guide 54. The guide 54 includes a guide path such as a lumen 56 for receiving a drill or K wire (not illustrated).

Each of the first retractor 18 and second retractor 20 may be provided with a connector 60, 62, respectively. The connector 60, 62 may comprise an aperture, post, snap or other connector for receiving a tie to connect to the backing plate 34. The tie may be elastic, and mounted under tension to place a radially outwardly bias on the connectors 60, 62 to maintain the soft tissue in the retracted orientation. In one implementation of the invention, a single elastic tie may be attached to a first connector, extended around the back of the backing plate, tensioned, and attached to the second connector.

Additional details of a backing plate 34 suited particularly for the wrist are illustrated in FIG. 6A-6G.

Additional details of a soft tissue retractor are illustrated in FIGS. 7A-7D. The first retractor 18 comprises a support body 22 extending between a proximal end 70 and a distal end 72. A connector 76 is provided near the proximal end 70, such as for connection to a tie as has been discussed. The connector 76 may include a post 78 having one end connected to the support 22 and the other end carrying a closed loop or a transverse stop 80 which may reside in an aperture 82 in the support 22. An elastic tie may be looped around the post 78, and restrained from slipping off by the transverse stop. The elastic tie may be looped around the back of the wrist and connected to the corresponding connector on the second retractor, under tension, to pull the first and second retractors away from each other.

The radius engaging surface 24 is provided near the distal end 72, and is separated axially from the soft tissue retention surface 26 by an inflection 84. The soft tissue retention surface 26 may be provided with a greater width than the width of the radius engaging surface 24. In the illustrated implementation, radius engaging service 24 is provided on a projection 86 extending distally beyond the distal end of the guide structure 32, and having a maximum width of no more than about 70%, or no more than about 50% or less of the width of the soft tissue retention surface 26. The width of the projection tapers smaller in a distal direction to a rounded tip 88 which is spaced apart laterally from the longitudinal axis of the lumen 30.

FIGS. 8A-8B show additional details of a lunate retractor which also doubles as a drill guide. The drill guide 50 includes a proximal handle 52 adjacent the proximal end 90 of the drill guide 50. An angled or arcuate body 92 connects the proximal handle 52 and a tubular guide 94 containing a lumen 96 configured to axially removably receive either a drill or a bone anchor such as a K wire. The longitudinal axis of the lumen maybe at least about 45° and preferably between about 80 and 110° from the longitudinal axis of the proximal handle 52. This facilitates grasping the proximal handle 52 and pressing the distal end 54 against the radius when used as a drill guide, or against the lunate, when used for lunate fixation and retraction.

Figure 13A:
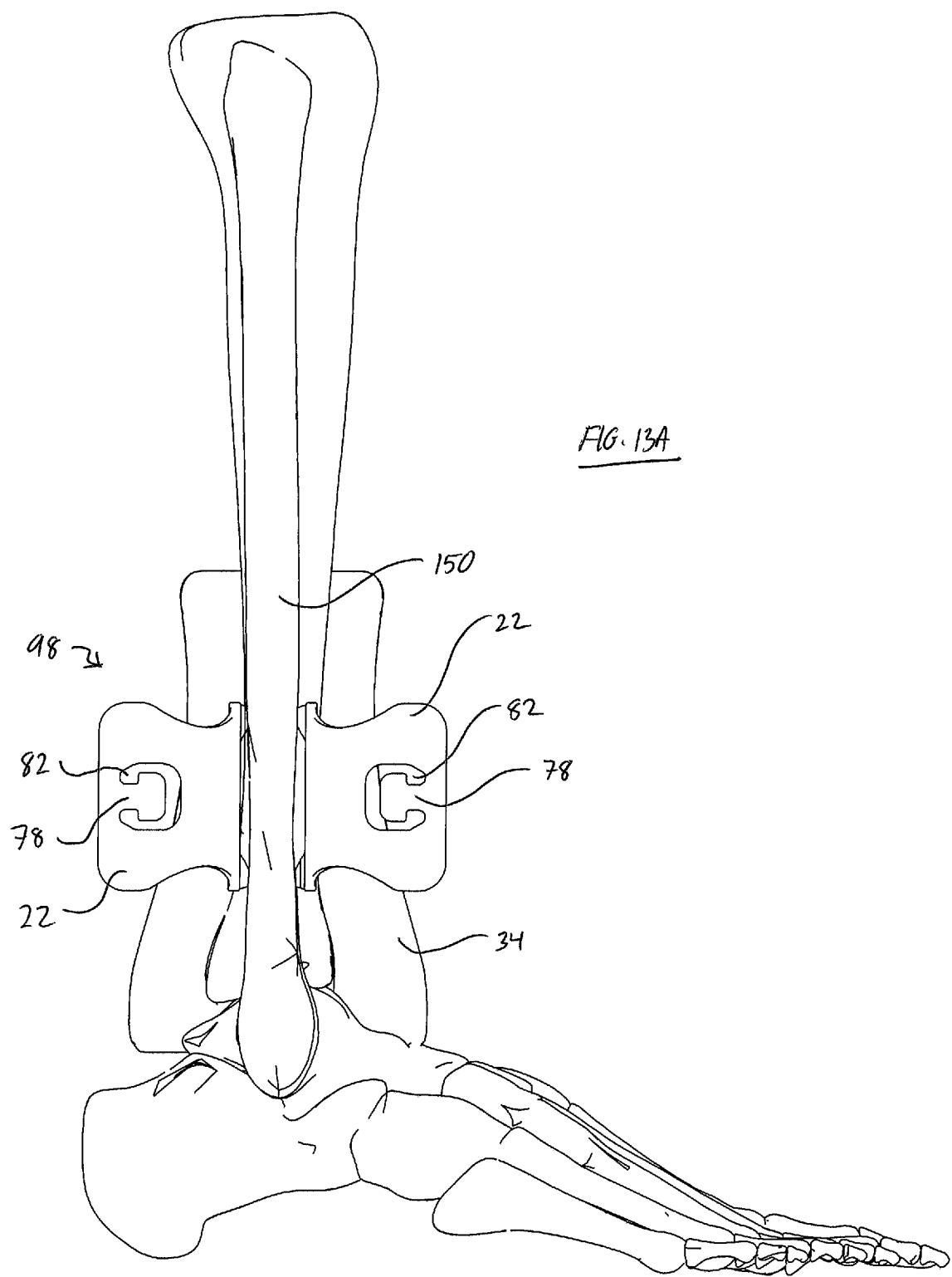
FIGS. 13A-13B illustrate a fibula retraction and stabilization system in relation to the ankle.
Figure 13B:
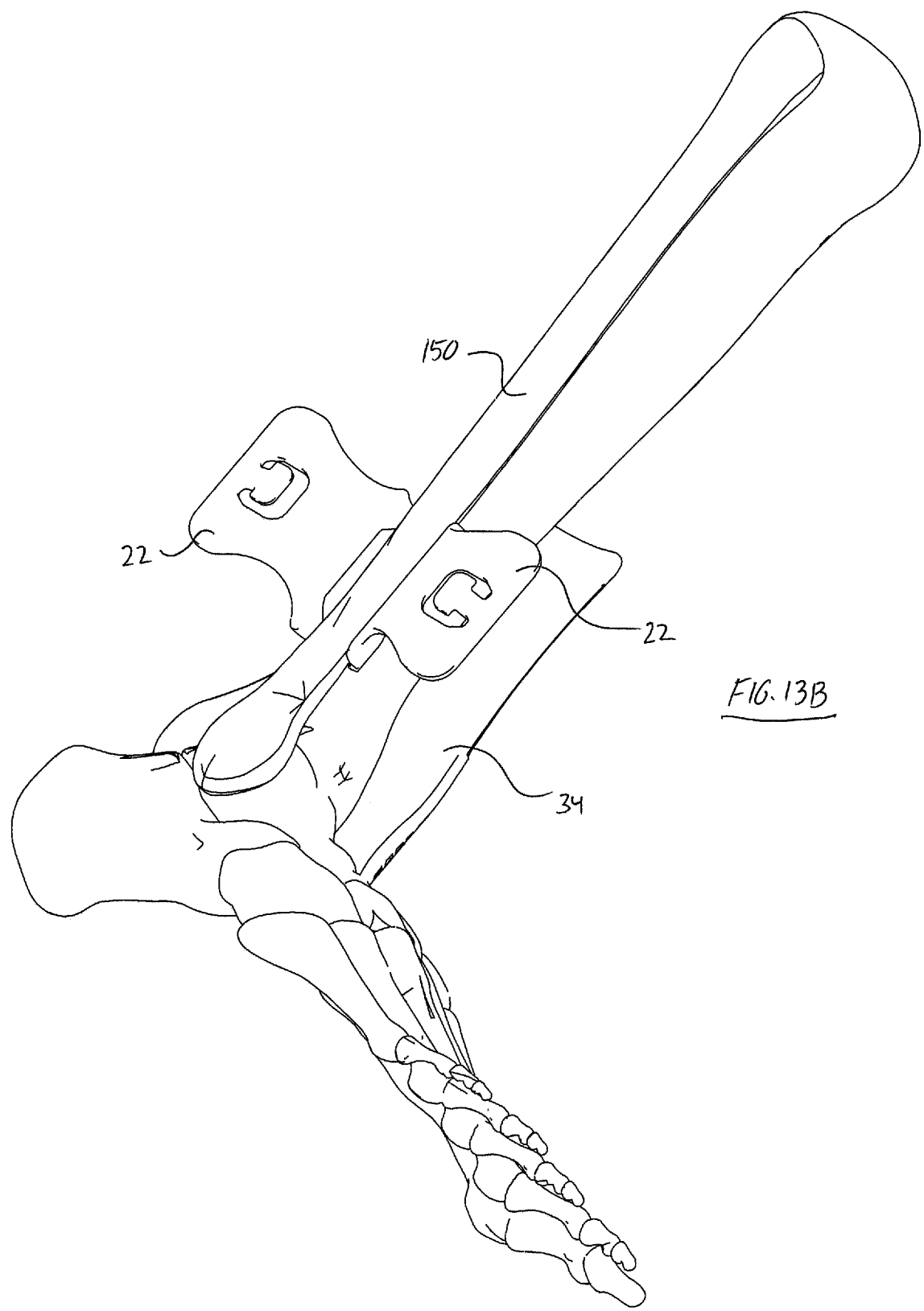

FIGS. 10A through 10C show details of a fibula retractor 98 utilized in an ankle repair procedure on a fibula 150. The fibula retractor 98 is similar to the wrist retractors illustrated previously, except that the distal end 72 of the support 22 is provided with a first distal projection 86 and a distinct second distal projection 100, spaced apart and configured to hook around the bone and resist torsional movement and facilitate increased surface area of the soft tissue contacting surface. Fibula retractors and corresponding backing plate are shown in relation to the ankle in FIGS. 13A-13B, below.

Figure 11A:
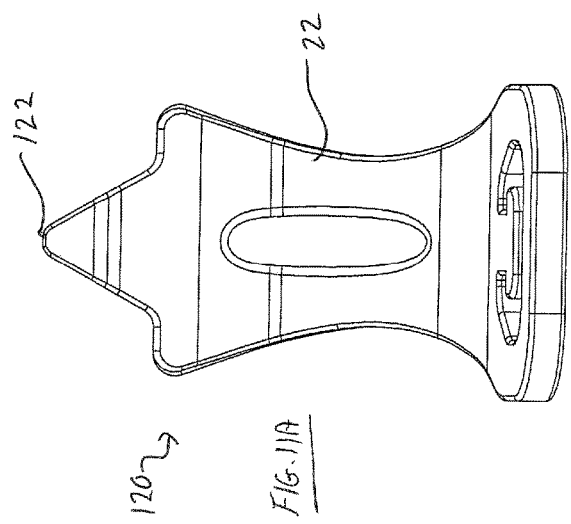
FIGS. 11A-11B are detail views of a soft tissue retractor configured for use on either side of an incision.
Figure 11B:
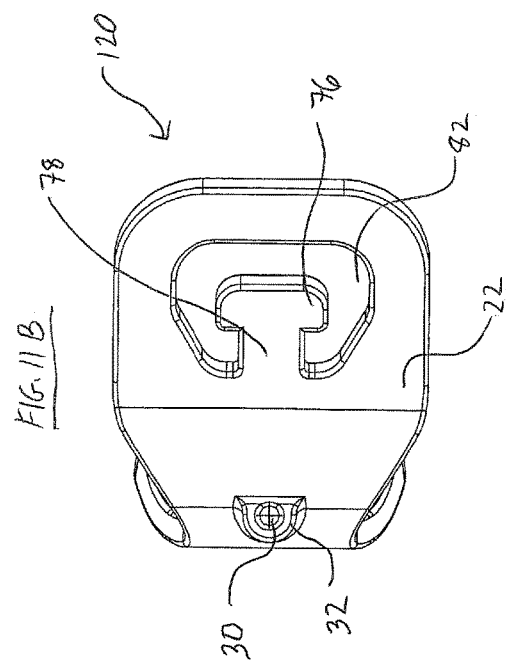

FIGS. 11A-11C illustrate an alternative universal soft tissue retractor 120 which is similar to retractors disclosed previously herein except that the universal retractor 120 can be used on either the right or left side of the incision while previously disclosed retractors were configured for separate left and right side placement. One structural distinction for the universal retractor 120 is the relationship between the K-wire lumen 30 and the tip 122. In use a surgeon may sink the K-wire through the lumen 30 and into the bone, then a twisting moment is created when the previously described retractor is rotated around the K-wire to engage the tip 122. For the universal retractor 120, the intent is to engage the tip 122, then angle back and secure the K-wire. But they are both aligned along a central longitudinal axis of the body 22, so no twisting moment is created.

The proximal portion of the retractor (see, e.g., FIG. 7B) has a longitudinal axis that is at a non normal angle to the longitudinal axis of the K-wire lumen. This is designed to allow the proximal portion of the retractor to reside close to horizontal to the table plane, extending away from the incision and out of the way of the surgeon. This proximal portion acts as a lever which the elastics are always pulling down to keep them out of the way for the surgeon and to keep the retraction of the tissue tight.

FIGS. 12A through 12C illustrate details of a dual headed lunate fixation tool and drill guide 130. The dual headed lunate offers the use of two different profiles. A first profile has a bulbous working end 132 which engages more linear length of the incision compared to the second narrow working end engages less. A first guide lumen 134 is provided at a first end 136 and a second guide lumen 138 is provided at a second end 140 of the drill guide 130. The first and second guide lumen may be substantially parallel to each other and joined by a handle portion 142. The drill guide 130 provides the surgeon with two different bone engaging surfaces and drill guide geometry from which to select in a given procedure.

Procedure steps in an exemplary procedure are described below. Not all steps are necessary in a particular procedure, multiple images may be obtained depending on the nature of the fracture(s), and the order of performance of some of the steps can be varied as will be understood by those of skill in the art.

Take the Backing Plate out of the pouch.
Place Backing Plate on the patient's forearm.
Establish surgical access to the radius.
Take one of the Ulnar side retractors out of the pouch.
Drill the K wire at the desired angle using the handheld radiolucent drill guide.
Slide Ulnar side retractor passing the K-wire through the guide lumen into desired position. Ensure the tip is distal to the guide lumen. Alternatively, insert the ulnar side retractor first, securing the distal tip under the bone. Then insert the K-wire into the lumen and drill into the bone.
Take the Radial side retractor out of the pouch.
Drill the K wire at the desired angle using the handheld radiolucent drill guide.
Slide Radial side retractor passing the K-wire through the guide lumen into desired position. Ensure the tip is distal to the guide lumen.
Secure both Ulnar, Radial, and Backing plate with rubber bands.
If more visualization of the lunate region is needed, use the retractor end of the handheld radiolucent drill guide as a retraction mechanism.
Place implant plate on the space between the two Ulnar fixed parts over the radius
Check where plate was placed relative to the fixed device parts.
Once implant plate is positioned, put some acumen K-wire (2 K wires placed, using the handheld radiolucent drill guide), to hold the plate in position.
Clamp backing plate to the bone.
Place another K wire (Trajectory K wire).
Take imaging shot (Xray with contrast) to judge plate's position with respect to radial bone. Verify bone fragments are correctly positioned to ensure proper range of motion for the patient once healed.
Move the setup until obtaining a proper shot by grabbing onto the clamp.
Drive trajectory k wire forward/backwards or change trajectory as needed.
Reposition the clamp accordingly to get a better view.
Repeat the shot as needed.
Remove K-wires.
Remove rubber bands.
Remove Ulnar and Radial parts.
Remove Backing plate.
Standard surgical closure.

Additional details of a variety of system components are illustrated in the attached Figures, with structural details of specific examples identified in the table below and associated with call out numbers in the drawings. All recited dimensions are related to specific embodiments, but any such recited dimension may be varied by +/−25% or +/−15% or other scaling depending upon the desired application and performance as will be understood by those of skill in the art. Method steps are also described below the feature table, below.

| ID | Feature | Description | Specification range |
|---|---|---|---|
| 1 | Wrist Backing plate | Base Curvature | Curvature that matches the contour of the forearm to allow for arm resting on the plate. | Defined by four arc segments with radii 34, 44, 30, and 40 mm. |

-continued

| ID | Feature | Description | Specification range |
|---|---|---|---|
| 2 | Side Cuts | Two symmetric side cuts for matching forearm shape and ensuring good support and contact. Cuts are symmetric for device to be used for both left and right arms. | Hourglass shaped Width of the plate at proximal end: 54.52 mm. Width of the plate at distal end: 78.8 mm. Width of the plate at neck: 57.6 mm. Cut: 40 mm width at proximal end 17.43 mm width at distal end |
| 3 | Distal wings | Optimized degree of radial/ulnar coverage. | 144° of coverage (wing-to-wing) in one implementation; generally within the range of from about 90 to 180 degrees |
| 4 | Length | Optimal length to provide good structural support of forearm. | 160 mm. |
| 5 | Fillet | Fillet corners to smooth the edges No sharp surfaces to irritate patient skin or represent sharp points for gloves. | Radius of 10 mm at distal, 8 mm at proximal end, and 1 mm throughout. |
| 6 | Grid pattern | Covering the distal end, to improve the grip and allow for tunable clamp placement. | Rectangular pattern with 1 mm depth and contoured pockets; grid size may be from about 0.5 to about 2.0 mm |
| 7 | Thickness | Optimal thickness to decrease bulkiness while ensuring stiffness and strength | At proximal end: 3 mm At distal end: 4 mm; both generally within the range of from about 1 mm-4 mm |
| 8 | Material | Nylon 12 could ultimately have composite reinforcement | Tensile Modulus: 1620 MPa Tensile Strength: 48 MPa Flexural/Bending Modulus (23° C.): 1,500 MPa |
| 9 | Scale | Scaled to 0.8 on x and y axes for small size | Scaling factor: 0.8 |
| 10 Ulnar Plate (Left & Right) | Base Profile | Curved handle extending laterally away from the incision site so surgeon's view is un-obstructed. Length extended beyond wrist to create appropriate vector for elastic restraints | Defined by two 60° arcs with radii 25 mm and 28.3 mm, respectively. 20 mm long rectangular tail and 0.8 mm thick pointy end. |
| 11 | Tip | Tip created by a cut at the distal end. For better attachment of the plate within the bony structures. Offset from centerline of plate for torsional adjustments Geometry provides leverage | Width: 15.78 mm Height: 11.5 mm Fillet of 1.75 mm radius. |
| 12 | Rib | Cylindrical Rib structure appended on opposite side of the tip, with an inner hole for K-wire placement to secure the plates by drilling into the bone. Offset from centerline to aid in placement and rotation | Rib diameter: 6 mm Inner hole diameter: 2.2 mm Rib Length: 25 mm Chamfer: 0.5 mm distance and 45° |

-continued

| ID | Feature | Description | Specification range |
|---|---|---|---|
| 13 | Rounded corners at proximal end | To improve flexibility, reduce bulkiness and smooth the edges. | 9 mm radius. |
| 14 | Center cut | To improve flexibility when surgeon handles and fixates the plate at different positions. Narrow neck to reduce the impact to incision length | 23.05 mm radius 35 mm cut length Fillets of 6 and 8 mm of radius at edges of center cut. |
| 15 | Thickness | Not too thick to avoid bulkiness nor too thin so that it is too fragile | 3.3 mm in one implementation; generally within the range of from about 1-4 mm |
| 16 | Hook | Located at the proximal end. To enable elastic band attachment. | 12 mm wide, 8.6 mm long hook over 18.9 mm wide, 13.6 mm long gap. Radius of Hook arcs: 2.5 mm and 1.5 mm |
| 17 | Material | Nylon 12 could ultimately have composite reinforcement | Tensile Modulus: 1620 MPa Tensile Strength: 48 MPa Flexural/Bending Modulus (23° C.): 1,500 MPa |
| 18 Lunate Retractor/ Drill Guide | Tip | Curved shape and flat end for optimal tissue contact without impingement risk | Two 60° arcs with radii 32 mm and 25 mm. Variable thickness: from 3.25 to 5.25 mm. Two 7.5- and 10-mm radii arcs at the distal end of the tip. |
| 19 | Cut-out | Cut-outs on sides of tip to confer hourglass shape | Cut-outs of 10.25- and 15-mm radii along length of tip. Width at proximal end: 16 mm Width at distal end: 14.49 mm |
| 20 | Fillet | Fillet corners to smooth the edges No sharp surfaces to irritate patient skin or represent sharp points for gloves. | 3 of radius surrounding entire part |
| 21 | Loft | Neck of the handle | Rectangular to oval shape. Loft constraint by two 40- and 70-mm radii arcs. |
| 22 | Rib | Rib cylindrical structure appended on same side of the retraction end, with an inner hole for K-wire placement to secure the plates by drilling into the bone. | Rib radius: 3.25 mm cylindrical rib of length 32.5 mm Inner hole radius: 1.10 mm Chamfer: 0.5 mm distance and 45° |
| 23 | Extrusion | Extrusion to increase the length of the retractor end | Length 52 mm in one implementation; generally from about 40-80 mm |
| 24 | Handle | Hole left that acts as handle for improved grip and potential interface with elastic restraints | 25-mm long, 6.5-mm wide cut with the shape of a slot in one implementation; length generally from about 20-50 mm |
| 25 | Fillet | Fillets along the rib for smoothing purposes. No sharp surfaces to | 0.5-mm fillets at chamfer 1 mm fillet along |

-continued

| ID | Feature | | Description | Specification range |
|---|---|---|---|---|
| | | | irritate patient skin or represent sharp points for gloves. | length of the rib |
| 26 | | Fillet | Fillets at the distal end and handle for smoothing purposes. No sharp surfaces to irritate patient skin or represent sharp points for gloves. | Radius 1 mm along tip width. Radius 2 mm along handle |
| 27 | | Duality | Dual device useful for both tissue retraction and as a drill guide for K-wire insertion | |
| 28 | Ankle Backing Plate | Base Curvature | Curvature that matches the contour of the _ to allow for _ resting on the plate. | Defined by four arc segments with radii 50, 54, 37.5, and 41.5 mm. |
| 29 | | Side Cuts | Two symmetric side cuts for matching _ shape and ensuring good support and contact. Cuts are symmetric for device to be used for both left and right legs. | Hourglass shaped Width of the plate at proximal end: 54.05 mm. Width of the plate at distal end: 78.89 mm. Width of the plate at neck: 50 mm. Cut: 40 mm width at proximal end 17.3 mm width at distal end |
| 30 | | Distal wings | Optimized degree of tibial coverage. | 144° of coverage (wing-to-wing) |
| 31 | | Length | Optimal length to provide good structural support of _. | 160 mm. |
| 32 | | Fillet | Fillet corners to smooth the edges No sharp surfaces to irritate patient skin or represent sharp points for gloves. | Radius of 10 mm at distal, 8 mm at proximal end, and 1 mm throughout. |
| 33 | | Grid pattern | Covering the _end, to improve the grip and allow for tunable clamp placement. | Rectangular pattern with 1 mm depth and contoured pockets |
| 34 | | Thickness | Optimal thickness to decrease bulkiness while ensuring stiffness and strength | At proximal end: 3 mm At distal end: 4 mm |
| 35 | | Material | Nylon 12 could ultimately have composite reinforcement | Tensile Modulus: 1620 MPa Tensile Strength: 48 MPa Flexural/Bending Modulus (23° C.): 1,500 MPa |
| 36 | Ankle side retractor | Base Profile | Curved handle extending laterally away from the incision site so surgeon's view is un-obstructed. Length extended beyond ankle to create appropriate vector for elastic restraints | Defined by two 60° arcs with radii 25 mm and 28.3 mm, respectively. 20 mm long rectangular tail and 0.8 mm thick pointy end. |
| 37 | | Tips | Two tips created, mirror images of each other, by a cut at the distal end. For better attachment of the plate within the bony structures. Geometry provides leverage | Width: 15.78 mm Height: 11.5 mm Fillet of 1.75 mm radius. |
| 38 | | Rounded corners at proximal end | To improve flexibility, reduce bulkiness and smooth the edges. | 9 mm radius. |

-continued

| ID | | Feature | Description | Specification range |
|---|---|---|---|---|
| 39 | | Side Relieves | Two center cuts on each side. To improve flexibility when surgeon handles and fixates the plate at different positions. Narrow neck to reduce the impact to incision length | 22.5 mm radius 35 mm cut length Fillets of 5 mm of radius at edges of center cut |
| 40 | | Thickness | Not too thick to avoid bulkiness nor too thin so that it is too fragile | 3.3 mm |
| 41 | | Hook | Located at the proximal end. To enable elastic band attachment. Slightly bend outwards to aid in rubber band placement. | Tilted 25.5° outward. 16 mm wide, 15.2 mm long hook over 22 mm wide, 20 mm long gap. Radius of Hook arcs: 4 mm and 1 mm |
| 42 | | Material | Nylon 12 could ultimately have composite reinforcement | Tensile Modulus: 1620 MPa Tensile Strength: 48 MPa Flexural/Bending Modulus (23° C.): 1,500 MPa |
| 43 | System | Tightening mechanism | Grid pattern improving grip for clamping at different locations. | |
| 44 | | Compatibility | k-wires and clamps | |
| 45 | | Adjustability after anchoring | Variable tensioning with elastic bands to easily adjust positions | |
| 46 | Clinical | Position verification | Device made of Nylon which is radiolucent, position can be verified during fluoroscopy imaging. | |
| 47 | | Variants of location | Different scales for different patient sizes. | |
| 48 | | Radiolucency | Materials transparent to X-rays | |
| 49 | | Hands free | Self-retaining mechanism via elastic bands and clamp placement | |
| 50 | | Permanent thru procedure | Self-retaining mechanism via elastic bands and clamp placement | |

What is claimed is:

1. A stabilizing retractor system for distal radius fracture repair, comprising:
   a backing plate configured to support the back of the wrist, the backing plate having a first side accessible on a first side of the wrist, a second side accessible on a second side of the wrist and a longitudinal axis; and
   at least a first soft tissue retractor comprising a first support body having a first radius engaging concavity on a first side on a distal portion of the body, and a first soft tissue retracting surface on a second side, proximal to the radius engaging concavity.

2. A stabilizing retractor system as in claim 1 further comprising a second soft tissue retractor comprising a second support body having a second radius engaging concavity on a first side and a second soft tissue retracting surface on a second side.

3. A stabilizing retractor system as in claim 1, further comprising a guide on the first soft tissue retractor, configured to direct a wire across the first radius engaging surface to anchor in the radius when positioned within the radius engaging concavity.

4. A stabilizing retractor system as in claim 3, wherein the guide comprises a lumen.

5. A stabilizing retractor system as in claim 4 wherein the lumen extends through the first support body.

6. A stabilizing retractor system as in claim 4, wherein the lumen extends through a guide structure carried by the first support body.

7. A stabilizing retractor system as in claim 4 wherein the lumen extends along an axis that intersects a surface of the radius in an intended use orientation at an angle that is within about 15 degrees of perpendicular to the surface of the radius.

8. A stabilizing retractor system as in claim 7 wherein the axis of the lumen is substantially perpendicular to the surface of the radius.

9. A stabilizing retractor system as in claim 2, further comprising a connector on each of the first and second soft tissue retractors.

10. A stabilizing retractor system as in claim 9, further comprising a tie for attaching the connectors around a back of the wrist and biasing the first and second soft tissue retractors apart from each other.

11. A stabilizing retractor system as in claim 10, wherein the tie is elastic.

12. A stabilizing retractor system as in claim 1, wherein the backing plate has a convex side and a concave side.

13. A stabilizing retractor system as in claim 12, further comprising first and second opposing forceps landing zones on the convex side, configured to facilitate grasping of the retractor system with forceps.

14. A stabilizing retractor system as in claim 13, wherein the landing zones comprise an anti-slip surface for enhancing attachment of the forceps.

15. A stabilizing retractor system as in claim 14, wherein the anti-slip surface comprises a plurality of surface deviations.

16. A stabilizing retractor system as in claim 15 wherein the deviations comprise a plurality of projections.

17. A stabilizing retractor system as in claim 15 wherein the deviations comprise a plurality of recesses.

18. A stabilizing retractor system as in claim 15 wherein the deviations comprise a plurality of apertures.

19. A stabilizing retractor system as in claim 1, wherein the soft tissue retractor is radiolucent.

20. A stabilizing retractor system as in claim 19, wherein the soft tissue retractor is formed by 3-D printing.

* * * * *